(12) United States Patent
Schoedel (10) Patent No.: US 6,927,062 B2
(45) Date of Patent: Aug. 9, 2005

(54) CONTROLS AND STANDARDS FOR ASSAYS AND METHOD FOR MANUFACTURE THEREOF

(75) Inventor: Barbara A. Schoedel, South Bend, IN (US)

(73) Assignee: Agdia, Inc., Elkhart, IN (US)

( * ) Notice: Subject to any disclaimer, the term of this patent is extended or adjusted under 35 U.S.C. 154(b) by 149 days.

(21) Appl. No.: 10/303,947

(22) Filed: Nov. 25, 2002

(65) Prior Publication Data

US 2004/0101972 A1 May 27, 2004

(51) Int. Cl.[7] .............................................. G01N 31/00
(52) U.S. Cl. ........................ 436/8; 435/7.1; 435/7.92; 435/967; 436/15; 436/18; 436/169
(58) Field of Search ............................... 435/4, 5, 810, 435/967, 7.92, 7.1; 436/8, 518, 169, 531, 15, 18

(56) References Cited

U.S. PATENT DOCUMENTS

| | | | |
|---|---|---|---|
| 3,671,400 A | 6/1972 | Cekoric, Jr. et al. | |
| 3,975,162 A | 8/1976 | Renn | |
| 4,234,316 A | 11/1980 | Hevey | |
| 4,684,615 A | 8/1987 | Hoskins | |
| 4,734,360 A | 3/1988 | Phillips | |
| 4,803,171 A | 2/1989 | Baier et al. | |
| 4,820,644 A | 4/1989 | Schafer et al. | |
| 4,834,234 A | * | 5/1989 | Sacherer et al. ............ 206/204 |

(Continued)

FOREIGN PATENT DOCUMENTS

EP           0140489           5/1985

OTHER PUBLICATIONS

Stevens, Christine, Clinical Immunology and Serology, A Laboratory Perspective, 1996, pp. 7–10.*
Greenplate, Quantification of *Bacillus thuringiensis* insect Control Protein Cry1Ac Over Time in Bollgard Cotton Fruit and Terminals. Journal of Economic Entomology (1999) 92(6), 1377–1383.*
Greenstone, Bollworm or budworm? Squashblot immunoassay distinguished eggs of helicoverpa zea and Heliothis virescens, Journal of Economic Entomology (1995) vol. 88, No. 2, pp. 213–218.*
Zdunek et al., Transpot and accumlation rates of abscisic acid and aldehyde oxidase activity in Pisum sativum L. in response to suboptimal growth conditions, Journal of Experimental Botany, vol. 52, No. 359, pp. 1269–1276, Jun. 2001.*

*Primary Examiner*—Long V. Le
*Assistant Examiner*—Gary W. Counts
(74) *Attorney, Agent, or Firm*—Ian C. McLeod (57) ABSTRACT

Controls and standards for assays and method for manufacturing the controls and standards is described. The controls or standards comprise a porous carrier material which has quantitatively reversibly absorbed and dried thereon an analyte for the control or standard wherein the analyte is not degraded over time while it is absorbed to the porous carrier material. Preferably, the controls and standards are provided as a control strip (10) in which the porous carrier material (20) is adhered to the distal end (16) of a support member (12). To quantitatively elute the analyte from the carrier to a solvent for an assay, the carrier is contacted to the same solvent used for the samples in the assay. After the analyte has been eluted, the carrier is discarded and the assay is performed. The controls and standards are useful for assays which detect bacteria, fungi, viruses, and proteins.

22 Claims, 5 Drawing Sheets

U.S. PATENT DOCUMENTS

| | | | |
|---|---|---|---|
| 4,891,319 A | 1/1990 | Roser | |
| 5,009,994 A | 4/1991 | McGeehan | |
| 5,030,560 A | 7/1991 | Sinor et al. | |
| 5,098,893 A | 3/1992 | Franks et al. | |
| 5,118,609 A | 6/1992 | Baier et al. | |
| 5,126,242 A | 6/1992 | Hachmann et al. | |
| 5,149,653 A | 9/1992 | Roser | |
| 5,200,399 A | 4/1993 | Wettlaufer et al. | |
| 5,240,843 A | 8/1993 | Gibson et al. | |
| 5,290,765 A | 3/1994 | Wettlaufer et al. | |
| 5,292,507 A | 3/1994 | Charley | |
| 5,300,424 A | 4/1994 | Hoss et al. | |
| 5,403,706 A | 4/1995 | Wilk et al. | |
| 5,547,873 A | 8/1996 | Magneson et al. | |
| 5,571,667 A * | 11/1996 | Chu et al. | 435/5 |
| 5,728,574 A | 3/1998 | Legg | |
| 5,736,335 A * | 4/1998 | Emmons et al. | 435/6 |
| 5,955,448 A | 9/1999 | Colaco et al. | |
| 6,008,052 A | 12/1999 | Davis et al. | |
| 6,165,773 A | 12/2000 | New et al. | |
| 6,165,981 A * | 12/2000 | Flaa et al. | 514/21 |
| 6,168,957 B1 | 1/2001 | Matzinger et al. | |
| 6,258,045 B1 * | 7/2001 | Ray et al. | 600/573 |
| 6,281,004 B1 | 8/2001 | Bogen et al. | |
| 6,313,102 B1 | 11/2001 | Colaco et al. | |
| 6,528,325 B1 * | 3/2003 | Hubscher et al. | 436/518 |
| 6,686,170 B1 * | 2/2004 | Flanders et al. | 435/7.34 |
| 2002/0172937 A1 * | 11/2002 | Dave et al. | 435/5 |
| 2003/0068665 A1 * | 4/2003 | Kawamura et al. | 435/7.93 |
| 2003/0125208 A1 * | 7/2003 | Charudattan et al. | 504/117 |
| 2004/0033160 A1 * | 2/2004 | MacPhee et al. | 422/22 |
| 2004/0048359 A1 * | 3/2004 | Schmeling | 435/287.1 |

* cited by examiner

CONTROLS AND STANDARDS FOR ASSAYS AND METHOD FOR MANUFACTURE THEREOF

CROSS-REFERENCE TO RELATED APPLICATION

Not applicable.

STATEMENT REGARDING FEDERALLY SPONSORED RESEARCH OR DEVELOPMENT

Not applicable.

REFERENCE TO A "COMPUTER LISTING APPENDIX SUBMITTED ON A COMPACT DISC".

Not Applicable.

BACKGROUND OF THE INVENTION (1) Field of the Invention

The present invention relates to controls and standards for assays and methods for manufacturing the controls and standards. The controls or standards comprise a porous carrier material which has quantitatively reversibly absorbed thereon an analyte for the control or standard wherein the analyte is not significantly degraded over time while it is absorbed to the porous carrier material. Preferably, the controls and standards are provided as a control strip in which the porous carrier material is adhered to the distal end of a support member. The controls and standards are stable for prolonged periods of time and are useful for immunoassays which detect bacteria, fungi, viruses, and other antigens.

(2) Description of Related Art

Controls or standards are important components for most analytic assays. For many assays, particularly assays which use biological controls or standards, the controls or standards are provided as a freeze-dried material which is reconstituted to the proper concentration in an aqueous solution appropriate for the particular material. An aliquot of the reconstituted material is then diluted in an aqueous solution appropriate for the assay. The remainder of the reconstituted material is usually divided into aliquots which are then stored frozen or for particularly unstable material, discarded. For other assays that use biological material, the controls or standards are provided as a frozen solution or suspension which prior to use is thawed and an aliquot removed which is then diluted to the appropriate concentration for use in the assay. The remainder of the thawed material is refrozen for future use.

Regardless with how the material for the controls or standards is provided, there are two problems. The first is that the actual concentration of the material will vary from assay to assay because of pipetting errors which can occur during reconstitution of the material, dilution of the material, and aliquoting and dispensing the material. This uncertainty can make it difficult to correlate results from assay to assay, which can be important when the assays are quantitative. This problem is particularly acute when the assays are performed by different people.

The second problem is related to storage and stability of the material. Many biological materials are unstable when stored for extended periods either lyophilized or in aqueous solutions at a temperature above freezing, particularly when diluted to a concentration suitable for the assay. When stored at temperatures below freezing, many biological materials are susceptible to degradation when they are repeatedly frozen and then thawed. Therefore, the actual concentration of the biological material decreases over time which introduces an uncertainty into the assay that can make it difficult to correlate results from assay to assay, which can be important when the assays are quantitative. A further disadvantage is that storing frozen aqueous solutions of biological material requires expensive freezers that are preferably able to store the biological material at −80° C.

The prior art has attempted to address the above problems either by introducing methods for drying and storing biological materials which do not involve lyophilization or freezing or methods which attempt to avoid errors introduced by pipetting.

The following U.S. Patents disclose methods for drying a biological material without using lyophilization: U.S. Pat. No. 4,684,615 to Hoskins; U.S. Pat. Nos. 4,891,319 and 5,149,653, both to Roser; U.S. Pat. No. 5,009,994 to McGeehan; U.S. Pat. No. 5,030,560 to Sinor et al.; U.S. Pat. No. 5,098,893 to Franks et al.; U.S. Pat. Nos. 5,200,399 and 5,290,765, both to Wettlaufer et al.; U.S. Pat. No. 5,292,507 to Charley; U.S. Pat. No. 5,547,873 to Magneson et al., U.S. Pat. Nos. 5,955,448; U.S. Pat. No. 6,008,052 to Davis et al., and, 6,313,102 B1, both to Colaco et al. In general, the above methods involve mixing the biological material in a solution comprising inter alia a carbohydrate and drying the mixture at a temperature above freezing. The methods render the material stable at temperatures above freezing.

The following also disclose methods for preserving a biological material using agents other than a carbohydrate as the stabilizing agent: U.S. Pat. No. 5,240,843 to Gibson et al.; U.S. Pat. No. 5,126,242 to Hachmann et al.; U.S. Pat. No. 5,300,424 to Hoss et al.; U.S. Pat. No. 5,728,574 to Legg; and, U.S. Pat. No. 6,165,773 to New et al.

The following U.S. patents disclose devices for providing a reagent to an assay or use as controls for an assay and methods for manufacturing the devices.

U.S. Pat. No. 3,671,400 to Cekoric, Jr. et al. discloses bacterial controls for test procedures and reagents comprising discrete droplets of a nutrient gelatin and bacteria which has been vacuum desiccated at ambient temperature onto a sterile non-adhering supporting surface.

U.S. Pat. No. 3,975,162 to Renn discloses a device for providing a measured quantity of water-soluble or water-dispersible reagent to a water-containing solid medium is provided in the form consisting essentially of a film-forming solid organic binder which is at least partly soluble in water and having dispersed therein a measured quantity of the reagent.

U.S. Pat. No. 4,234,316 to Hevy discloses a device for delivering precise measured quantities of a plurality of reagents into an assay. The device comprises a water impervious support secured to one or more faces of which are discrete and separate elements each containing a water soluble or dispersible binder which has dispersed therein the reagent. The device is contacted with the assay medium for a time sufficient to dissolve the binder to release the reagent into the assay medium.

U.S. Pat. Nos. 4,803,171 and 5,118,609, both to Baier et al. disclose a carrier fleece for use as a reagent carrier from which reagents can be dissolved in an assay such as an immunological analysis. The carrier fleece comprises cellulose-containing fibers, polymer fibers, and an organic binding agent which has a hydroxyl or ester group, or both. Preferably, the binding agent is polyvinyl alcohol or polyacrylic esters.

U.S. Pat. No. 5,403,706 to Wilk et al. discloses a carrier matrix with a dissolvably impregnated reagent. The matrix is manufactured by slurring glass fibers with an excess of water and polyvinyl alcohol and forming a layer wherein all of the glass fibers are coated with the polyvinyl alcohol. The slurry layer is dried and then impregnated with the reagent. In use, the impregnated layer is contacted with a solvent which elutes the reagent from the layer.

U.S. Pat. No. 6,008,052 to Davis et al. discloses a method for preserving cells as controls or standards in cellular analysis. The cells are fixed with a fixative, reduced with a Schiff's base reducing agent, and then dried in the presence of a protein stabilizing compound such as trehalose.

U.S. Pat. No. 6,281,044 B1 to Bogen et al. discloses quality control devices for assays which measure analytes in cells and tissue samples comprising a matrix afixed with synthetic controls in different concentrations, or different synthetic controls. The matrix preferably includes an adhesive surface on the back side which adheres the matrix to a removable backing sheet which is removed when an assay is performed on the device. In use, the matrix is reacted with the same detection reagent used in the assay.

Only of minimal interest are U.S. Pat. No. 4,734,360 to Phillips (test strip for detecting ethanol); U.S. Pat. No. 4,820,644 to Schäfer et al. (porous carrier material containing first and second components of an immune reaction precipitated thereon); U.S. Pat. No. 6,168,957 B1 to Matzinger et al. (dry phase reagent test strip for measuring the concentration of an analyte); and, European Patent Application No. 0140489 to Sakata et al. (method for stabilizing immunologically active substances immobilized on an insoluble carrier).

While there are a number of methods for preserving analytes and there are several methods for providing controls or standards to assays, there still remains a need for a method for providing controls or standards for assays which is facile and inexpensive to prepare and which provide consistent results between assays regardless of the skill of the user of the control or standards or the time which has elapsed between assays. The present invention provides a method for providing controls or standards which satisfies the above need.

SUMMARY OF THE INVENTION

The present invention provides controls and standards for assays and methods for manufacturing the controls and standards. The controls or standards comprise a porous carrier material which has quantitatively reversibly absorbed and dried thereon an analyte for the control or standard wherein the analyte is not significantly degraded over time while it is absorbed to and dried on the porous carrier material. Preferably, the controls and standards are provided as a control strip in which the porous carrier material is adhered to the distal end of a support member. To quantitatively elute the analyte from the carrier for use in an assay, the carrier is contacted to or immersed in the same solvent used for the samples in the assay for a time sufficient to quantitatively elute the analyte into the solvent. After the analyte has been eluted, the carrier is discarded and the assay is performed. The controls and standards are stable over time at room temperature and 4° C. and are particularly useful for providing controls or standards to immunoassays for detecting bacteria, fungi, viruses, and proteins.

Therefore, in one aspect, the present invention provides a method for preparing a control or standard for a solution for an assay for detecting an analyte in a sample wherein the control or standard includes a dried form of the analyte which is not substantially degradable over time, which comprises (a) providing a porous carrier material; (b) contacting the porous carrier material to a solution containing a known concentration of the analyte for a time sufficient to impregnate the pretreated porous carrier material with the solution containing the analyte; and (c) removing the porous carrier material from the solution containing the analyte and drying in air to quantitatively reversibly bind the analyte to the porous carrier material to produce the control or standard wherein the dried form of the analyte is not substantially degradable over time.

Preferably, the porous carrier material comprises a material selected from the group consisting of nylon and glass fiber.

In a preferred embodiment of the method, the porous carrier material is adhered to a surface of a first end of a planar support member having a first end and an opposite end and which preferably comprises a polymer. In a further embodiment, the porous carrier material adhered to the surface of the support member is cut into strips after step (b) which are then held together side-by-side before contacting with the buffered salt solution containing the analyte in step (c) or the porous carrier material adhered to the surface of the support member is cut into strips after step (c).

In a further embodiment of the present invention, the solution containing the analyte includes one or more components selected from the group consisting of physiological buffers, salts, carrier proteins, non-ionic surfactants, and carbohydrates, which enables the analyte to resist substantial degradation for about 90 days at 4° C. and which facilitates the quantitative reversible binding of the analyte to the porous carrier material.

In particular embodiments, the carrier proteins are selected from the group consisting of bovine serum albumin, chicken egg albumin, and milk proteins; the non-ionic surfactants are selected from the group consisting of alcohol ethoxylate surfactants, alkylphenol ethoxylate surfactants, alkyl polyglycoside surfactants, and sorbitan ester surfactants; and the carbohydrate is selected from the group consisting of monosaccharides, disaccharides, and cyclitols. In further embodiments, the solution containing the analyte further includes a preservative.

In another aspect of the present invention, prior to contacting the porous carrier material to the solution containing the analyte in step (b), the porous carrier material is contacted to a pretreatment solution for a time sufficient to impregnate the porous carrier material with the pretreatment solution and then air-drying to produce a pretreated porous carrier material which is contacted to the solution containing the analyte in step (b).

In particular embodiments of the second aspect, the pretreatment solution includes one or more components selected from the group consisting of physiological buffers, salts, carrier proteins, non-ionic surfactants, and carbohydrates, which facilitates the quantitative reversible binding of the analyte to the porous carrier material; the carrier proteins are selected from the group consisting of bovine serum albumin, chicken egg albumin, and milk proteins; the non-ionic surfactants are selected from the group consisting of alcohol ethoxylate surfactants, alkylphenol ethoxylate surfactants, alkyl polyglycoside surfactants, and sorbitan ester surfactants; and, the carbohydrate is selected from the group consisting of monosaccharides, disaccharides, and cyclitols. In further embodiments, the pretreatment solution further includes a preservative.

In particular embodiments of the second aspect, the solution containing the analyte includes one or more components selected from the group consisting of physiological buffers, salts, carrier proteins, and carbohydrates, which enables the analyte to resist substantial degradation for about 90 days at 4° C. in particular embodiments, the carrier proteins are selected from the group consisting of bovine serum albumin, chicken egg albumin, and milk proteins; the carbohydrate is selected from the group consisting of monosaccharides, disaccharides, and cyclitols. In further embodiments, the solution further containing the analyte further includes a preservative.

In a further embodiment of the second aspect, the pretreatment solution includes a physiological buffer, at least one of KCl and NaCl, bovine serum albumin, and polyoxyethylenesorbitan monolaurate and in a further still embodiment, the solution containing the analyte includes a physiological buffer, at least one of KCl and NaCl, chicken egg albumin, and mannitol.

In a further still embodiment of the second aspect, the pretreatment solution includes a physiological buffer, at least one of KCl and NaCl, and sucrose and in a further still embodiment, the solution containing the analyte includes a physiological buffer and at least one of KCl and NaCl.

In particular embodiments of any one of the above embodiments or aspects, the analyte is a pathogen selected from the group consisting of bacteria, fungi, virus, parasite, and pest. In further embodiments, the pathogen is a plant pathogen which in one way can be obtained from the sap of a plant infected with the pathogen or by recombinant DNA technology. In particular embodiments, it is preferable that the pathogen is inactivated.

In a further embodiment, the analyte is a recombinant protein produced by a transgenic plant which by way of example can be a recombinant protein selected from the group consisting of Bt-Cry1Ac, Bt-CryAb, Bt-Cry3A, Bt-Cry9C, and neomycin phosphotransferase.

In a further embodiment, the analyte can comprise at least one protein from eggs of a plant pest which plant pest by way of example can be selected from the group consisting of cotton bollworm and tobacco budworm.

In a further embodiment, the analyte is a hormone which by way of example can be a plant hormone selected from the group consisting of abscisic acid, dihydrozeatin riboside, indole-3-acetic acid, isopentenyladenosine, and trans-zeatin riboside.

In a further still embodiment, the analyte is an isolated protein from a pathogen selected from the group consisting of bacteria, fungi, virus, parasite, and pest which is preferably produced in a bacterium. In particular embodiments, the pathogen is a plant pathogen.

In a further still embodiment, the analyte is an antigen or metabolite produced by a cancer cell or an antigen or metabolite produced by a patient with an autoimmune disease.

In a further still embodiment, the assay is an immunoassay selected from the group consisting of ELISA, immunoprecipitation, immunodiffusion, radioimmunoassay, immunofluorescence, and lateral flow.

Thus, in light of the above method, the present invention further provides a control or standard for an assay for detecting an analyte in a sample, which comprises a porous support impregnated with the analyte prepared using the above described method. The control or standard is particularly useful for an assay selected from the group consisting of ELISA, immunoprecipitation, immunodiffusion, immunofluorescence, radioimmunoassays, and lateral flow.

Further still, the present invention provides a kit for providing a control or standard for a solution assay for detecting an analyte in a sample, which comprises (a) a plurality of porous supports impregnated with the analyte prepared according to the method described above; and (b) a desiccant. The kit is particularly useful for an assay selected from the group consisting of ELISA, immunoprecipitation, immunodiffusion, radioimmunoassays, immunofluorescence assays, and lateral flow. In a further embodiment, the assay is an ELISA for the analyte and the kit further includes the ELISA.

Thus, in light of the above controls and standards, the present invention further provides a method for performing a solution assay for determining whether a test sample contains an analyte, which comprises which comprises (a) providing at least one porous support impregnated with the analyte which is prepared as in any one of Claims 1 to 42; (b) contacting the impregnated porous support with a sample buffer for a time sufficient to quantitatively elute the quantitatively reversibly bound analyte from the porous support to provide a control sample for the assay; and (c) performing the assay with the control sample.

In a further embodiment of the method, the porous support is removed from the sample buffer after the analyte has been eluted from the porous support.

In a further still embodiment of the method, a sample suspected of containing the analyte is diluted in the sample buffer to provide a test sample for the assay.

In a further still embodiment of the method, after performing the assay with the control sample and the test sample determining whether the test sample contains the analyte by comparing the assay results produced by the test sample to the results produced by the control sample wherein similar results indicate that the test sample contains the analyte. In a further embodiment, the control sample and the test sample are serially diluted to provide a series of dilutions for the assay.

The above method is particularly useful for an assay selected from the group consisting of ELISA, immunoprecipitation, immunodiffusion, and lateral flow.

Objects

The object of the present invention is to provide controls and standards for assays that are easy to prepare, stable at ambient temperatures, and simple to use.

It is a further object of the present invention to provide controls and standards which are standardized to provide consistent results between assays regardless of the user using the control or standard or the time between assays.

These and other objects of the present invention will become increasingly apparent with reference to the following drawings and preferred embodiments.

DETAILED DESCRIPTION OF THE INVENTION

All patents, patent applications, government publications, government regulations, and literature references cited in this specification are hereby incorporated herein by reference in their entirety. In case of conflict, the present description, including definitions, will control.

The present invention provides novel controls and standards for assays and methods for manufacturing the controls and standards. The controls or standards comprise a porous carrier material impregnated with a solution of an analyte which is then air dried at room temperature. The method produces a control or standard wherein the analyte is quantitatively reversibly absorbed to the porous carrier material. The porous carrier material is then divided into a plurality of controls or standards, wherein each individual control or standard contains the same amount of analyte. The controls and standards can then be conveniently stored for long periods of time over a wide range of temperatures without substantial degradation. When the porous carrier material is adhered to a support member, the support member facilitates the handling and use of the controls and standards. When the porous carrier material impregnated with the analyte is contacted to or immersed in a solvent, the analyte is quantitatively released into the solvent. The controls and standards of the present invention are particularly useful for assays in which a control or standard is to be provided to the assay in a solution.

As used herein, the terms "quantitatively reversibly absorbed" and "quantitatively reversibly bound" mean that the analyte impregnating and air dried to the porous carrier material is not immobilized thereon or permanently bound thereto. Instead, the analyte can be quantitatively eluted from the carrier material when the carrier material with the analyte thereon is contacted to a solvent. This means that the amount of analyte elutable from the carrier material is substantially consistent from control or standard to control or standard. In other words, the amount of analyte delivered by each control or standard of the present invention is measurable and reproducible. In the case of controls, there is lot-to-lot reproducibility. That is, from assay to assay, the user of the control can be confident that the amount of analyte eluted from the carrier material from one lot in one assay is correlatable to the amount of analyte eluted from the carrier material from the same or another lot in another assay at the same time or at another time and further correlatable to the amount of analyte eluted from the carrier from the same or another lot in a further assay performed by another user. In the case of standards, there is lot-only reproducibility. That is, from assay to assay for any particular lot of standard, the user of the standard can be confident that the amount of analyte eluted from the carrier material in one assay is correlatable to the amount of analyte eluted from the carrier material of the same lot in another assay at the same time or at another time and further correlatable to the amount of analyte eluted from the carrier of the same lot in a further assay performed by another user.

The controls or standards are substantially stable when stored at 4° C. or room temperature for an extended period of time. In general, substantially stable over time means that over a time period of about 30 days at room temperature, there is about less than 20%, preferably less than 10%, degradation or destabilization of the analyte and at 4° C., there is about less than 20%, preferably less than 10%, degradation or destabilization of the analyte. In general. The method for manufacturing the controls or standards does not require specialized equipment such as lyophilizers to dry the analyte during manufacture. In addition, the method produces controls or standards which do not require specialized freezers for storing the controls or standards after they have been made.

The controls and standards of the present invention have the following characteristics: (1) the controls and standards are standardized such that all users have the exact same control or standard and all controls and standards quantitatively release the analyte when contacted to a buffer for eluting the analyte, (2) the controls and standards are easy to use, (3) the method for manufacturing the controls and standards is inexpensive which enables the controls or standards to be provided to users at low cost, (4) the method for manufacturing the controls and standards enables sufficient quantities of the exact same controls or standards to be made at one time to ensure that the exact same control or standard is available for many years, and (5) the standards and controls are stable (do not substantially degrade) over prolonged or extended time periods at elevated temperatures such as 37° C., room temperature, or under refrigeration or temperatures below 0° C. Preferably, the analyte comprising the control or standard is not substantially degraded or destabilized for at least 90 days at 4° C. Thus, the present invention provides standardized, practical controls and standards for a variety of assays. The present invention is particularly useful for providing a plurality of bacterial, viral, or isolated protein controls and antigen standards for immunoassays which use a sample in solution such as enzyme-linked immunosorbant assays (ELISAs). The present invention is also useful for providing controls and standards for other types of assays which use a sample in a solution such as chromatographic assays, electrophoretic assays, polymerase chain reaction (PCR) assays, and any other assay which requires the use of controls and which would benefit from the use of controls which have been standardized.

The general method for preparing the controls and standards is as follows. A porous carrier material is provided which is impregnated with a solution comprising an analyte which is to serve as a control or standard for an assay, by contacting the porous carrier material to the solution comprising the analyte. The porous carrier material impregnated with the analyte is then air dried at room temperature which quantitatively reversibly absorbs the analyte to the porous carrier material-the analyte is not immobilized on the porous carrier material so as to permanently bind it to the porous carrier material. The porous carrier material with the analyte dried thereon is then divided into a plurality of controls or standards. Each of the plurality of controls or standards can then be used to provide the analyte quantitatively reversibly absorbed thereon to an assay by immersing the porous carrier material with the analyte thereon in the same solvent as is used for the sample to be analyzed in the assay for a time sufficient to quantitatively elute the analyte from the porous carrier material.

For example, to provide a bacterial or viral control for an ELISA, a porous carrier material to which the bacteria or virus is quantitatively reversibly absorbed is incubated in the same sample solvent as is to be used for the samples to be analyzed by the ELISA for a time sufficient to quantitatively elute the bacteria or virus into the sample solvent. After the bacteria or virus has been eluted from the porous carrier material, the porous carrier material can be removed from the sample solvent and the ELISA performed according to the particular protocol for the ELISA.

The porous carrier material can comprise any water-insoluble porous material commonly used for absorbing or filtering analytes. The porous carrier material is preferably a matrix comprised of interconnected, liquid permeable hollow spaces. Such materials are usually made of glass, synthetic resins or natural, synthetic, organic, or inorganic polymers, or paper. The porous carrier material is preferably planar and preferably comprises glass fibers or a synthetic polymer such as a polyamide polymer (nylon), polystyrene, polypropylene, polyvinyl chloride, or the like. Most preferably, the porous carrier material comprises glass fibers or nylon. An example of a nylon porous carrier material which has been used to produce controls and standards includes, but is not limited to, the nylon porous carrier material available from Schleicher & Schuell. Examples of glass fiber porous carrier materials include, but are not limited to, the Millipore T9BM0515 and GFCP203000 glass fiber carrier materials available from Millipore Corp., Bedford, Mass., the Schleicher & Schuell #33 glass fiber carrier material available from Schleicher & Schuell, Keene, N.H., and the Whatman Rapid Q27 available from Whatman, Inc., Newton, Mass.

While a solution comprising the analyte can be applied directly to the porous carrier material, in a preferred embodiment, the porous carrier material is preferably pretreated with a pretreatment solution to reduce irreversible adsorption of the analyte to the porous carrier material to facilitate quantitative elution of the analyte from the porous carrier material (facilitates quantitative reversible binding of the analyte to the porous carrier material) and to reduce the likelihood of substantial degradation of the analyte over time. To pretreat the porous carrier material, the porous carrier material is impregnated with the pretreatment solution by contacting the porous carrier material to the pretreatment solution for time sufficient to soak the porous carrier material and then air dried at room temperature. Afterwards, the pretreated porous carrier material is impregnated with a solution comprising an analyte by contacting the pretreated porous carrier material to the solution comprising the analyte to impregnate the pretreated porous carrier material and then air dried at room temperature.

Preferably, the pretreatment solution is a buffered solution comprising one or more carbohydrates selected from the group consisting of monosaccharides, disaccharides, and cyclitols, and optionally, a protein such as bovine serum albumin, chicken egg albumin, or a mixture of proteins such as those found in milk. The carbohydrates which are useful include those selected from the group consisting of glucose, sucrose, trehalose, raffinose, sorbose, xylose, sorbitol, arabinose, cellobiose, fructose, galactose, myoinositol, lactose, lyxose, maltose, mannitol, and mannose. The most preferred carbohydrate is sucrose. Optionally, the pretreatment solution can further include one or more of non-ionic surfactants which include, but are not limited to, alcohol ethoxylate surfactants, alkylphenol ethoxylate surfactants, alkyl polyglycoside surfactants, and sorbitan ester surfactants such as polyoxyethylene sorbitan monolaurate; one or more salts such as sodium chloride or potassium chloride; and a preservative such as sodium azide. Preferably, the pretreatment solution has a pH between about pH 6.5 and pH 8.0 and comprises a biological buffer such as a phosphate, tris-HCl, MOPS, HEPES, PIPES, tricine, ACES, or the like.

Figure 1A:
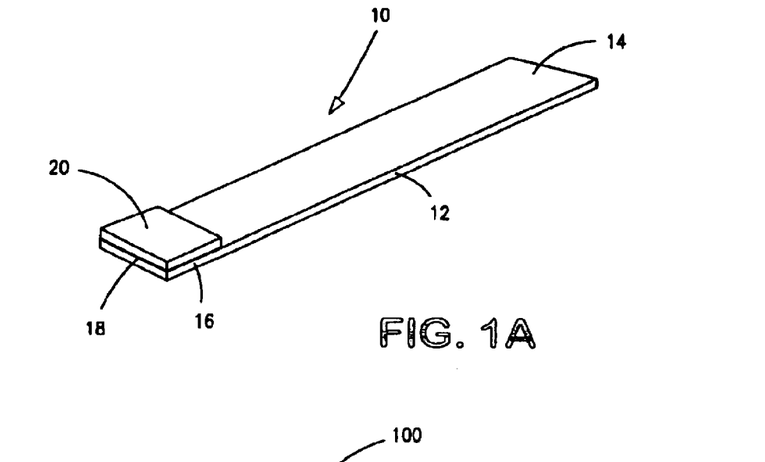
FIG. 1A shows a perspective view of a control strip 10 showing porous carrier material 20 adhered to the distal end 16 of support member 12.
Figure 1B:
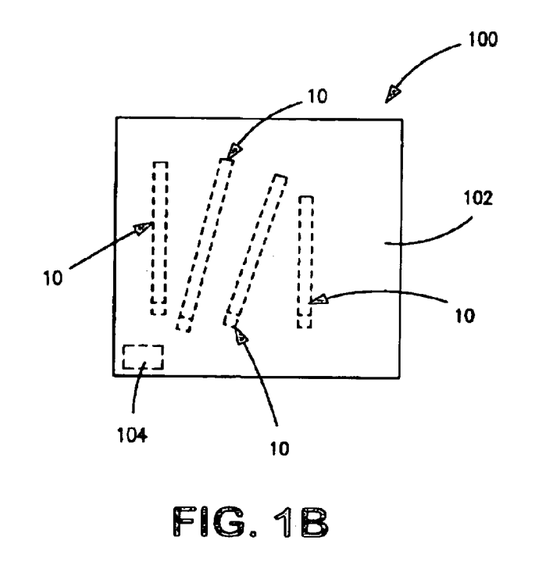
FIG. 1B shows a front view of a kit 100 comprising a package 102 with a plurality of control strips 10 disposed therein.
Figure 1C:
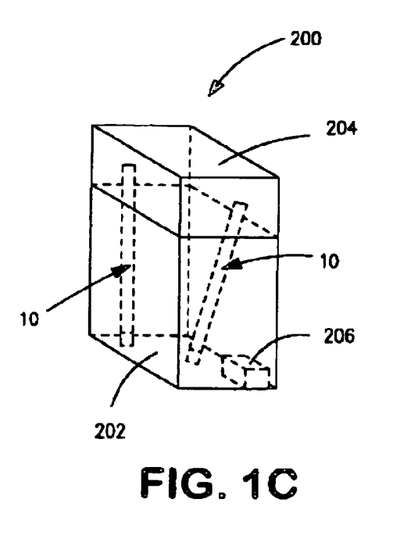
FIG. 1C shows a perspective view of kit 200 comprising a rigid container 202 with a plurality of control strips disposed therein.

A preferred pretreatment solution for pretreating a porous carrier material for receiving bacteria or virus comprises a buffer, a protein such as albumin, a non-ionic surfactant, and a preservative. In a more preferred embodiment, a suitable pretreatment solution comprises a phosphate buffer at a physiological pH of about 7.4, bovine serum albumin, polyoxyethylene sorbitan monolaurate, and sodium azide. For example, a pretreatment solution which can be used to pretreat porous carrier material prior to adding bacteria or virus to the carrier comprises 40 mM dibasic sodium phosphate, 9.5 mM monobasic sodium phosphate, 0.1% (w/v) bovine serum albumin, 0.1% (w/v) polyoxyethylene sorbitan monolaurate, and 3 mM sodium azide.

A preferred pretreatment solution for pretreating a porous carrier material for receiving isolated proteins comprises a buffer, one or more salts, and a carbohydrate. In a more preferred embodiment, a suitable pretreatment solution comprises a phosphate buffer, sucrose, sodium chloride, and potassium chloride. For example, a pretreatment buffer which can be used to pretreat porous carrier material prior to adding the isolated protein to the carrier comprises 8.2 mM dibasic sodium phosphate, 1.5 mM monobasic sodium phosphate, 15% (w/v) sucrose, 2.7 mM potassium chloride, and 137 mM sodium chloride.

The analyte solution comprising the analyte comprises a buffer containing one or more salts. The analyte solution can optionally contain one or more carbohydrates selected from the group consisting of monosaccharides, disaccharides, and cyclitols, a protein such chicken egg albumin or a mixture of proteins such as those found in milk, one or more salts, and a preservative. The carbohydrates which are useful include those selected from the group consisting of glucose, sucrose, trehalose, raffinose, sorbose, xylose, sorbitol, arabinose, cellobiose, fructose, galactose, myo-inositol, lactose, lyxose, maltose, mannitol, and mannose. The most preferred carbohydrate is mannitol. Preferably, the analyte solution has a pH between about pH 6.5 and pH 8.0 and comprises a biological buffer such as that provided by a phosphate, Tris-HCl, Bis-Tris, MES, ADA, MOPSO, Bis-Tris propane, BES, TES, DIPSO, TAPSO, HEPPSO, POPSO, EPPS, TEA, bicine, TAPS, AMPSO, CHES, CAPSO, AMP, CAPS, MOPS, HEPES, PIPES, tricine, ACES, or the like, buffer. The components comprising the analyte solution reduce irreversible adsorption of the analyte to the porous carrier material to facilitate quantitative elution of the analyte from the porous carrier material (facilitates quantitative reversible binding of the analyte to the porous carrier material) and to reduce the likelihood of substantial degradation of the analyte over time. Thus, the solution not only facilitates the quantitative elution of the analyte from the porous carrier material but also reduces substantial degradation of the analyte over time.

A preferred analyte solution for bacteria, virus, or pest comprises a buffer, a protein such as chicken egg albumin, one or more salts, a carbohydrate, and a preservative. In a more preferred embodiment, the analyte solution comprises a phosphate buffer, sodium chloride, potassium chloride, chicken egg albumin, mannitol, and sodium azide. For example, a suitable analyte solution which can used for bacteria or virus comprises 8 mM dibasic sodium phosphate, 1.5 mM monobasic sodium phosphate, 2.7 mM potassium chloride, 137 mM sodium chloride, 10 mM sodium sulfite, 0.2% (w/v) chicken egg albumin, 110 mM mannitol, and 3 mM sodium azide.

A preferred analyte solution for isolated proteins, including hormones, which can also be used for bacteria, comprises a buffer and one or more salts. In a most preferred embodiment, the analyte solution comprises a phosphate buffer, potassium chloride, and sodium chloride. For example, a suitable analyte solution for isolated proteins or bacteria which can be used comprises 8.2 mM dibasic sodium phosphate, 1.5 mM monobasic sodium phosphate, 2.7 mM potassium chloride, and 137 mM sodium chloride.

In particular embodiments of controls or standards comprising a pathogen, it can be necessary to inactivate the pathogen either before it is absorbed to the porous carrier material of after it has been absorbed to the porous carrier material. There are a plurality of methods for inactivating pathogens, particularly viruses. These methods include, but are not limited to, heat inactivation or treating a solution containing the pathogen with formalin, binary ethyleneimine (BEI), aziridines such as ethyleneimine and N-acetylethyleneimine, olive leaf extract, and pokeweed sap. The above methods and other methods for inactivating pathogens are well known in the art.

In a preferred embodiment of the control or standard, the porous carrier material is supported on a support member which provides the control or standard as a control strip (or stick or device). The support member preferably comprises a polymer or other non-absorbent material such as plastic card stock. FIG. 1A shows a perspective view of the preferred embodiment. The control strip 10 consists of a support member 12 with a proximal end 14 and a distal end 16. The distal end 16 of the control strip 10 has an adhesive layer 18 to which is adhered the porous carrier material 20 to which the analyte (not shown) is impregnated thereon. This embodiment of the control or standard enables it to be easily handled. The user can grasp the control strip 10 at the proximal end 14 of the support member 12 and immerse the porous carrier material 20 containing the analyte in the appropriate assay solution for a time sufficient to elute the analyte from the porous carrier material 20. For example, for use in an ELISA, the control strip 10 enables the porous carrier material 20 containing the analyte to be immersed in ELISA extraction solution in a well of an ELISA plate while resting the support member 12 against the side of the well during the elution period. After the analyte has been eluted from the porous carrier material 20, the user can remove the porous carrier material 20 from the extraction solution by grasping the proximal end 14 of the support member 12. A convenient method for preparing controls and standards comprising the control strip 10 is described in Example 1.

The controls and standards of the present invention can be provided in a kit comprising a package containing a plurality of the controls or standards, preferably in the form of controls strips 10. FIG. 1B illustrates one embodiment of a kit. The kit 100 consists of a package 102 which has disposed therein a plurality of control strips 10. Optionally, the kit 100 further includes a desiccant 104 disposed within the package 102. Preferably, the package 102 is a pouch made of a material that is impervious to light and moisture. A suitable pouch is a foil-lined plastic ZIPLOCK bag. The control strips 10 can be disposed within the package as individual units as shown or connected together with tape (not shown) or perforations (not shown). In another embodiment shown in FIG. 1C, the kit 200 consists of a rigid container 202 with a removable closure 204 in which are disposed a plurality of the control strips 10. Preferably, the rigid container 202 is impervious to light and moisture. Optionally, the kit 200 further includes a desiccant 206 disposed within the rigid container 202. In an embodiment not shown, the closure 204 can further include an opening (not shown) with a lid (not shown) adjacent thereto which enables the user to shake out control strips 10 when the lid is removed from the opening. In a further embodiment, the controls and standards can also be provided as a component of a kit for an immunoassay, preferably a kit for an ELISA, wherein the controls or standards are in a package 102, rigid container 202, or the like, which contains a plurality of the controls or standards, preferably in the form of controls strips 10.

The present invention is particularly useful for providing controls and standards for a variety of assays of human or veterinary importance for detecting diseases caused by viruses, bacteria, fungi, parasites, and the like. For example, assays for detecting diseases of human importance which would benefit from controls or standards prepared according to the method of the present invention include, but are not limited to, assays for detecting antigens of or antibodies against toxosidiois, rubella, CVM, herpes simplex virus (1 or 2), *Chlamydia, H. pylori*, Syphilis, *Brucella*, tuberculosis, measles, mumps, VZV, influenza, parainfluenza, adenovirus, leptospira, HTLV, Epstein Barr virus, respiratory syncytial virus, VLA, *varicella, streptococcus*, mononucleosis, malaria, hepatitis, typhoid, *Echinococcus, Cysticerosis*, amoebiasis, *Candida, E. coli* 0157, *E. coli* verotoxin, rotavirus, *staphylococcus*, and meningitis. Assays for detecting other human diseases of importance which would benefit from controls or standards prepared according to the method of the present invention include, but are not limited to, assays for detecting various cancer antigens such as alpha-feto protein, carcinoembryonic antigen, prostrate specific antigens, human chorionic gonadotropin, and the like.

Assays for detecting diseases of veterinary importance which would benefit from controls or standards prepared according to the method of the present invention include, but are not limited to, assays for detecting particular antigens of or particular antibodies against feline leukemia virus, feline herpesvirus, leishmania, heart worm, canine parvovirus, hog cholera, pseudorabies, parainfluenza virus, porcine reproductive and respiratory syndrom virus, porcine influenza, *Eryspelothix rhusiopathic*, bovine respiratory syncytial virus, bovine viral diarrhea virus, adenovirus 3, *Faciola hepatica*, rotavirus, coronavirus, Cryptosporidium, bovine herpesvirus, viral haemorrhagic septicaemia, infectious haematopoietic necrosis, infections pancreatic necrosis, spring viraema of carp, *Chlamydia psittaci, Mycoplasma agalactiae*, infectious laryngotracheitis virus, turkey rhinotracheitis, and Marek's disease virus.

The method of the present invention can also provide controls and standards for assays for detecting cytokines; assays for detecting cardiac markers such as myoglobin, troponins, and the like; assays for detecting autoimmune markers such as anti-nuclear antibody (ANA), anti-double-stranded DNA antibody, anti-SmRNA antibody, rheumatoid factor, and the like; assays for detecting various drugs in a test subject such as cotinine, opiates, and the like; and, assays for determining thyroid, hormone, and fertility profiles of a patient.

While the present invention is useful for providing controls and standards for assays of human or veterinary importance, the present invention is particularly useful for providing controls and standards for immunoassays which detect plant pathogens, particularly ELISAs. The following is a list of important bacterial, viral, and fungal plant pathogens for which there are immunoassays for detecting the pathogens and for which controls or standards made according to the present invention would be useful.

Plant Viruses

African Cassava Mosaic Virus (ACMV)
Alfalfa Mosaic Virus (AMV)
Alstroemeria Mosaic Virus (AlMV)
American Plum Line Pattern Virus (APLPV)
Andean Potato Latent Virus (APLV)
Apple Chlorotic Leaf Spot Virus (ACLSV)
Apple Mosaic Virus (ApMV)
Arabis Mosaic Virus (ArMV)
Asparagus Virus 2 (AV2)
Banana Bract Mosaic Virus (BBrMV)
Banana Bunchy Top Virus (BBTV)
Banana Streak Virus (BSV)
Barley Stripe Mosaic Virus (BSMV)
Barley Yellow Dwarf Virus-mav (BYDV-mav)
Barley Yellow Dwarf Virus-pav (BYDV-pav)
Barley Yellow Dwarf Virus-rmv (BYDV-rmv)
Barley Yellow Dwarf Virus-rpv (BYDV-rpv)
Barley Yellow Dwarf Virus-sgv (BYDV-sgv)
Bean Common Mosaic Virus (BCMV)
Bean Pod Mottle Virus (BPMV)
Bean Yellow Mosaic Virus (BYMV)
Beet Necrotic Yellow Vein Virus BNYVV
Beet Western Yellows Virus (BWYV)
Blueberry Leaf Mottle Virus (BLMV)
Blueberry Shock Virus (BlShV)
Blueberry Scorch Virus (BBScV)
Blueberry Shoestring Virus (BSSV)
Broad Bean Wilt Virus (BBWV)
Brome Mosaic Virus (BMV)
Calibrachoa Mottle Virus (CbMV)
Carnation Etched Ring Virus (CERV)
Carnation Latent Virus (CLV)
Carnation Mottle Virus (CarMV)
Carnation Necrotic Fleck Virus (CNFV)
Carnation Ringspot Virus (CRSV)
Cauliflower Mosaic Virus (CaMV)
Cherry Leaf Roll Virus (CLRV)
Chrysanthemum Chlorotic Mottle Viroid (CChMVd)
Chrysanthemum Stunt Viroid (CSVd)
Chrysanthemum Virus B (CVB)
Citrus Tristeza Virus (CTV)
Cowpea Mosaic Virus (CPMV)
Cucumber Green Mottle Mosaic Virus (CGMMV)
Cucumber Mosaic Virus (CMV)
Cucumber Mosaic Virus—Subgroup I (CMV I)
Cucumber Mosaic Virus—Subgroup II (CMV II)
Cymbidium Mosaic Virus (CyMV)
Cymbidium Ringspot Virus (CyRSV)
Dasheen Mosaic Virus (DsMV)
Garlic Common Latent Virus (GCLV)
Geminiviruses—3F7 (3F7)
Grapevine Fanleaf Virus (GFLV)
Grapevine Fleck Virus (GFkV)
Grapevine Leaf Roll Virus 1 (GLRV 1)
Grapevine Leaf Roll Virus 2 (GLRV 2)
Grapevine Leaf Roll Virus 3 (GLRV 3)
Grapevine Leaf Roll Virus 5 (GLRV 5)
Grapevine Leaf Roll Virus 7 (GLRV 7)
Grapevine Virus A (GVA)
Groundnut Bud Necrosis Virus (GBNV)
Groundnut Ringspot Virus (GRSV)
Hibiscus Chlorotic Ringspot Virus (HCRSV)
Hosta Virus X (HsVX)
Impatiens Necrotic Spot Virus (INSV)
Iris Yellow Spot Virus (IYSV)
Johnsongrass Mosaic Virus (JgMV)

Kalanchoe Latent Virus (KLV)
Kyuri Green Mottle Mosaic Virus (KGMMV)
Leek Yellow Stripe Virus (LYSV)
Lettuce Mosaic Virus (LMV)
Lily Symptomless Virus (LSV)
Maize Chlorotic Mottle Virus (MCMV)
Maize Dwarf Mosaic Virus (MDMV)
Maize Mosaic Virus (MMV)
Maize Stripe Virus (MSpV)
Maize White Line Mosaic Virus (MWLMV)
Melon Necrotic Spot Virus (MNSV)
Nandina Mosaic Virus (NaMV)
Odontoglossum Ringspot Virus (ORSV)
Onion Yellow Dwarf Virus (OYDV)
Papaya Mosaic Virus (PapMV)
Papaya Ringspot Virus (PRSV)
Pea Seed-borne Mosaic Virus (PSbMV)
Peach Rosette Mosaic Virus (PRMV)
Peanut Stunt Virus (PSV)
Pelargonium Flower Break Virus (PFBV)
Pelargonium Leaf Curl Virus (PLCV)
Pelargonium Zonate Spot Virus (PZSV)
Pepino Mosaic Virus (PepMV)
Pepper Mild Mottle Virus (PMMOV)
Pepper Mottle Virus (PepMoV)
Plum Pox Virus (PPV)
Poinsettia Mosaic Virus (PnMV)
Potato Aucuba Mosaic Virus (PAMV)
Potato Latent Virus (PotLV)
Potato Leaf Roll Virus (PLRV)
Potato Spindle Tuber Viroid (PSTVd)
Potato Virus A (PVA)
Potato Virus M (PVM)
Potato Virus S (PVS)
Potato Virus T (PVT)
Potato Virus V (PVV)
Potato Virus X (PVX)
Potato Virus Y (PVY)
Potato Virus Y-necrotic strain (PVY-n)
Potato Virus Y-strain o (PVY-o)
Potyvirus Group (POTY)
Prune Dwarf Virus (PDV)
Prunus Necrotic Ringspot Virus (PNRSV)
Raspberry Bushy Dwarf Virus (RBDV)
Raspberry Ringspot Virus (RpRSV)
Red LaSoda Virus (RLaSV)
Ribgrass Mosaic Virus (RMV)
Shallot Latent Virus (SLV)
Shallot Yellow Stripe Virus (SYSV)
Soil-borne Wheat Mosaic Virus (SBWMV)
Southern Bean Mosaic Virus (SBMV)
Soybean Mosaic Virus (SMV)
Squash Mosaic Virus (SqMV)
Stolbur MLO (SMLO)
Strawberry Latent Ringspot Virus (SLRSV)
Strawberry Mild Yellow Edge—associated Virus (SMYEaV)
Sugarcane Bacilliform Virus (SCBV)
Sugarcane Mosaic Virus (SCMV)
Tobacco Etch Virus (TEV)
Tobacco Mosaic Virus (TMV)
Tobacco Mosaic Virus-c (TMV-c)
Tobacco Rattle Virus (TRV)
Tobacco Ringspot Virus (TRSV)
Tobacco Streak Virus (TSV)
Tobacco Vein Mottling Virus (TVMV)
Tomato Aspermy Virus (TAV)
Tomato Black Ring Virus—S, G (TBRV)
Tomato Bushy Stunt Virus (TBSV)
Tomato Chlorotic Spot Virus (TCSV)
Tomato Mosaic Virus (TOMV)
Tomato Ringspot Virus (TORSV)
Tomato Spotted Wilt Virus (TSWV)
Tospovirus Group (TOSPO)
Turnip Mosaic Virus (TUMV)
Watermelon Mosaic Virus 2 (WMV2)
Wheat Dwarf Virus (WDV)
Wheat Spindle Streak Mosaic Virus (WSSMV)
Wheat Streak Mosaic Virus (WSMV)
Zucchini Yellow Mosaic Virus (ZYMV)

Plant Bacteria

*Acidovorax avenae* subsp. *citrulli* (Aac)
*Clavibacter michiganensis* subsp. *michiganensis* (Cmm)
*Clavibacter michiganensis* subsp. *nebraskensis* (Cmn)
*Clavibacter michiganensis* subsp. *sepedonicus* (Cms)
*Clavibacter michiganensis* subsp. *tessellarius* (Cmt)
Corn Stunt Spiroplasma (CSS)
*Erwinia amylovora* (Ea)
*Erwinia carotovora* (Ec)
*Erwinia carotovora* subsp. *atroseptica* (Eca)
*Erwinia chrysanthemi* (Echr)
*Erwinia stewartii* (Es)
*Pseudomonas avenae* (Pa)
*Pseudomonas fuscovaginae* (Pf)
*Pseudomonas glumae* (Pg)
*Pseudomonas syringae* pv. *phaseolicola* (Psph)
*Ralstonia solanacearum* (Rs)
*Spiroplasma citri* (Sc)
*Xanthomonas* (Xan)
*Xanthomonas albilineans* (Xalb)
*Xanthomonas campestris* pv. *armoraciae* (Xcarm)
*Xanthomonas campestris* pv. *begoniae* (Xcb)
*Xanthomonas campestris* pv. *campestris* (Xcc)
*Xanthomonas axonopodis* pv. *citri* (Xccit or Xacit)
*Xanthomonas campestris* pv. *dieffenbachiae* (Xcd)
*Xanthomonas campestris* pv. *oryzae* (Xco)
*Xanthomonas campestris* pv. *pelargonii* (Xcp)
*Xanthomonas campestris* pv. *phaseoli* (Xcph)
*Xanthomonas campestris* pv. *vesicatoria* (Xcv)
*Xanthomonas maltophilia* (Xm)
*Xylella fastidiosa* (Xf)

Plant Fungi

*Phytophthora* (Phyt)
*Verticillium dahlia* (Vdah)

Other plant viruses not mentioned herein are recited in the VIDE database published by CAB International Publishing, New York, N.Y. Other plant bacteria not mentioned herein are catalogued at the national Collection of Plant Bacteria at the Central Science Laboratory, Sand Hutton, York, United Kingdom. Other plant fungi not mentioned herein are recited in the U.S. National Fungus Collections database, Agricultural Research Service, Beltsville, Md.

In general, to produce a control or standard comprising any one of the above pathogens, the porous carrier material is impregnated with the whole virus, the whole bacteria, or an isolated protein produced by a recombinant microorganism using the method for impregnating porous carrier material with viruses, bacteria, or proteins as described previously and then air drying at room temperature.

In the case of whole plant viruses and bacteria, the whole virus or bacteria can be obtained from the sap of plants infected with the virus or bacteria. The infected sap is obtained by pressing the infected plant tissue (leaves, stems, or the like) to extrude the sap from the tissue. The infected sap is then mixed with the analyte solution and then diluted with analyte solution to the appropriate concentration for applying to the porous carrier material.

Alternatively, the infected tissue can be ground and lyophilized. To prepare the controls and standards, the lyophilized infected tissue can be suspended to the appropriate concentration in analyte solution and then applied to the porous carrier material. Particular viruses can be provided from tissue cultures infected with the virus and particular bacteria can be provided from bacterial cultures.

The present invention is also useful for providing controls or standards for immunoassays, particularly ELISAs, for identifying transgenic organisms such as transgenic plants or determining whether a particular product is produced by a transgenic organism or plant. The controls or standards include one or more of the particular identifying products or markers produced by the transgenic organism or plant. For example, to prepare a control or standard for detecting the Bt-Cry1Ab protein, the Bt-Cry1Ac protein, or both, the porous carrier material is impregnated with the Bt-Cry1Ab protein, the Bt-Cry1Ac protein, or both, using the method for impregnating porous carrier material with proteins as described previously and then air drying at room temperature. These proteins are expressed in transgenic crops such as cotton and corn varieties. As an another example, to prepare a control or standard for detecting the Bt-Cry3A protein which is produced in transgenic potato plants, the porous carrier material can be impregnated with the Bt-Cry3A protein using the method for impregnating porous carrier material with proteins as described previously and then air drying at room temperature. As a further example, to prepare a control or standard for detecting the Bt-Cry9C endotoxin which is produced in some varieties of transgenic corn, the porous carrier material can be impregnated with the Bt-Cry9C endotoxin using the method for impregnating porous carrier material with proteins as described previously and then air drying at room temperature. As a further example, to prepare a control or standard for detecting neomycin phosphotransferase II (NPII), a common marker used for making transgenic plants, the porous carrier material can be impregnated with the NPII using the method for impregnating porous carrier material with proteins as described previously and then air drying at room temperature.

The present invention is useful for providing controls or standards for immunoassays, particularly ELISAs, for detecting and quantifying various pests, in particular, plant pests such as the cotton bollworm and the tobacco budworm. For example, the eggs of the bollworm or budworm are crushed in phosphate buffered saline to make an extract which is used to impregnate the porous carrier material using the method for impregnating porous carrier material with proteins as described previously and then air drying at room temperature.

The present invention is useful for providing controls or standards for immunoassays, particularly ELISAs, for detecting and quantifying hormones produced by an organism, in particular, hormones produced by a plant such as plant growth hormones. For example, a control or standard for detecting and quantifying abscisic acid is provided by impregnating the porous carrier material with abscisic acid using the method for impregnating porous carrier material with proteins as described previously and then air drying at room temperature. As another example, a control or standard for detecting and quantifying dihydrozeatin riboside is provided by impregnating the porous carrier material with dihydrozeatin riboside using the method for impregnating porous carrier material with proteins as described previously and then air drying at room temperature. As another example, a control or standard for detecting and quantifying indole-3-acetic acid is provided by impregnating the porous carrier material with indole-3-acetic acid using the method for impregnating porous carrier material with proteins as described previously and then air drying at room temperature. As another example, a control or standard for detecting and quantifying isopentenyladenosine is provided by impregnating the porous carrier material with isopentenyladenosine using the method for impregnating porous carrier material with proteins as described previously and then air drying at room temperature. As another example, a control or standard for detecting and quantifying trans-zeatin riboside is provided by impregnating the porous carrier material with trans-zeatin riboside using the method for impregnating porous carrier material with proteins as described previously and then air drying at room temperature.

An example of solution assay for determining whether a test sample contains any one of the above analytes is as follows. At least one porous support impregnated with the analyte in an amount suitable for the assay is prepared as taught herein. The impregnated porous support is then contacted with or immersed in a sample buffer for a time sufficient to quantitatively elute the quantitatively reversibly bound analyte from the porous support to provide a control sample for the assay. The assay is then performed with the control sample in the manner appropriate for the particular assay. Preferably, after the analyte has been eluted from the porous support, the porous support is removed from the sample buffer.

Run parallel with the control is a test sample which comprises a sample suspected of containing the analyte which has been diluted in the sample buffer. After performing the assay with the control sample and the test sample, the assay results for each are compared to determine whether the test sample contains the analyte wherein similar results indicate that the test sample contains the analyte. In particular embodiments, the control sample and the test sample are serially diluted to provide a series of dilutions for the assay.

The following examples are intended to promote a further understanding of the present invention.

EXAMPLE 1

Preparation of control strips for the following examples was as follows.

Porous carrier material was cut into 4 mm wide strips. The carrier materials which were used comprised nylon pads (from Schleicher & Schuell) or glass fiber pads such as Whatman Rapid Q27, Schleicher & Schuell (S&S) #33, Millipore T9BM0515, or Millipore GFCP203000.

For treated porous carrier materials, the carrier materials were soaked briefly in pretreatment buffer 01 consisting of 40 mM dibasic sodium phosphate, 9.5 mM monobasic sodium phosphate, 0.1% (w/v) bovine serum albumin, 0.1% polyoxyethylenesorbitan monolaurate, and 3 mM sodium azide or in phosphate buffered sucrose consisting of 4.4 mM sucrose (about 15% (w/v)) in 8.2 mM dibasic sodium phosphate, 2.7 mM potassium chloride, 1.5 mM monobasic sodium phosphate, and 137 mM sodium chloride. Afterwards, the carrier materials were dried overnight at room temperature. In general, the carrier materials treated with pretreatment buffer were used for bacterial or viral control, the carrier materials treated with phosphate buffered sucrose was used for standards comprising isolated proteins, and untreated carrier materials were used for various bacterial controls.

The untreated or treated porous carrier materials were each adhered to plastic card stock having a 4 mm wide adhesive area extending the length of one side of the plastic card stock and having identifying information taped to the non-adhesive area. After adhering the carrier materials to the entire length of the adhesive area of the plastic card stock, the card stock was cut perpendicular to the adhesive area in 4 mm increments to produce a plurality of 4 mm wide strips, each strip having a 4 $mm^2$ section of the carrier material adhered thereto. The strips were then taped together side-by-side in lots of about twenty strips each.

The taped together strips were then swiped through a solution containing bacteria, virus, or protein at an appropriate concentration such that the porous carrier material was saturated with the solution. Afterwards, the strips were dried at room temperature overnight or longer and then packaged into moisture tight foil-lined ZIPLOCK bags containing a desiccant until needed. The strips were stored at a temperature between about −20 to 37° C. For most controls and standards, the preferred storage temperature was 4° C.

EXAMPLE 2

This example illustrates the method for making and using bacterial controls and standards for ELISAs using nylon pads as the porous carrier material.

*Xanthamonas campestris* pv. *pelargonii* (Xcp), a geranium pathogen was suspended in phosphate buffered saline (PBS: 8.2 mM dibasic sodium phosphate, 2.7 mM potassium chloride, 1.5 mM monobasic potassium phosphate, and 137 mM sodium chloride). Then, 5, 6, and 7 $\mu$L aliquots of the suspension were each applied to separate untreated nylon pads adhered to plastic card stock as described in Example 1. After allowing the nylon pads to dry overnight, each nylon pad on plastic card stock was cut into triplicate strips.

Each of the triplicate strips was placed in a well of an ELISA plate containing 100 $\mu$L of extraction buffer suitable for the plant tissue to be assayed. As a control, 5, 6, and 7 $\mu$L aliquots of the Xcp suspension were pipetted in triplicate wells containing the extraction buffer as well. After about two hours at room temperature, the strips were removed from the wells and the ELISA was performed as usual.

Figure 2:
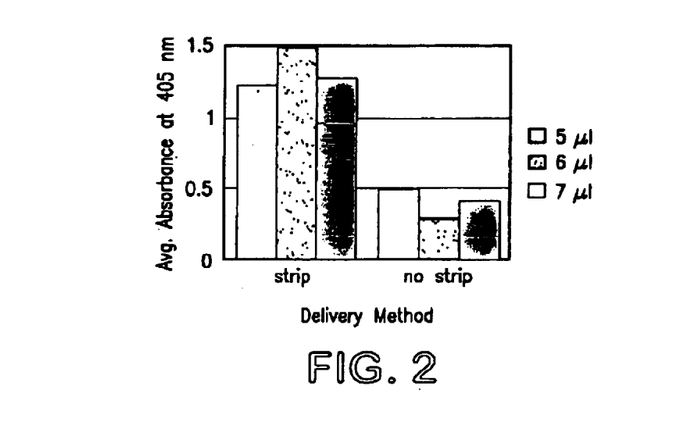
FIG. 2 is a bar chart of the results of ELISAs for detecting Xcp in which the Xcp was delivered to the ELISAs by control strips comprising nylon pads with the Xcp absorbed thereon compared to ELISAs in which the Xcp was delivered by pipetting.

FIG. 2 shows that the ELISA results with the Xcp controls added to the wells using the strips in which the Xcp had been dried thereon was significantly enhanced over that in which the Xcp suspension had been added directly to the well. The enhanced results may in part be due to the drying process which altered the bacteria in a way which allowed more of the epitope to be recognized by the antibody used for the ELISA. The results demonstrate that any species of bacteria or fungi can be delivered to ELISAs using the above untreated nylon pads adhered to plastic card stocks.

EXAMPLE 3

This example illustrates the method for making and using viral controls and standards for ELISAs using nylon pads. The viruses used in this example were obtained from lyophilized infected tissue.

Lyophilized impatiens necrotic spot virus (INSV) infected ornamental tissue and tomato spotted wilt virus (TSWV) infected tissue were each reconstituted in phosphate buffered saline (PBS) and in distilled water. Then, 10 $\mu$L aliquots of each suspension was applied to separate untreated nylon pads adhered to plastic card stock as described in Example 1. After allowing the nylon pads to dry overnight at room temperature, each was cut into triplicate strips.

Lyophilized arabis mosaic virus (ArMV) infected vinca tissue and potato virus M (PVM) were reconstituted in PBS and in distilled water. Then, 10 $\mu$L aliquots were applied to separate nylon pads pretreated with pretreatment buffer 01 and adhered to plastic card stock as described in Example 1. After allowing the nylon pads to dry overnight at room temperature, each was cut into triplicate strips.

Each of the triplicate strips was placed in a well of an ELISA plate containing 100 $\mu$L of extraction buffer appropriate for the plant tissue being assayed. As a control, 10 $\mu$L aliquots of the infected tissue suspensions were each pipetted in triplicate wells containing the extraction buffer as well. After about two hours at room temperature, the strips were removed from the wells and the ELISA was performed as usual. The ELISA plates were scored earlier than the test required to ensure numerical results.

Figure 3:
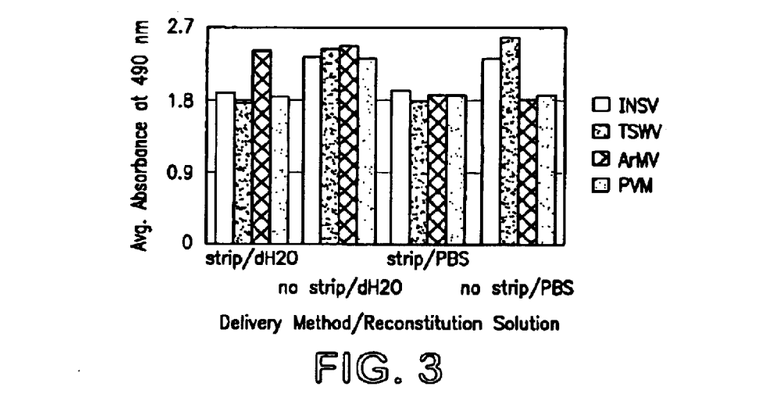
FIG. 3 is a bar chart of the results of ELISAs for detecting various viruses in which the various plant viruses were delivered to the ELISAs by control strips comprising nylon pads with the various viruses absorbed thereon compared to ELISAs in which the various plant viruses were delivered by pipetting.

As shown in FIG. 3, all of the infected tissues, each with a different viscosity, were effectively delivered to the ELISA test using either PBS or distilled water as the reconstitution fluid.

To determine whether the residence time of the strips in the ELISA wells could be reduced, 12 strips for each of INSV, TSWV, ArMV, and PVM made as above were each put into separate ELISA plate wells containing 100 $\mu$L extraction buffer. At one minute, ten minute, 30 minute, and 60 minute intervals, triplicate sets of each the strips were removed and the ELISA performed as usual.

Figure 4:
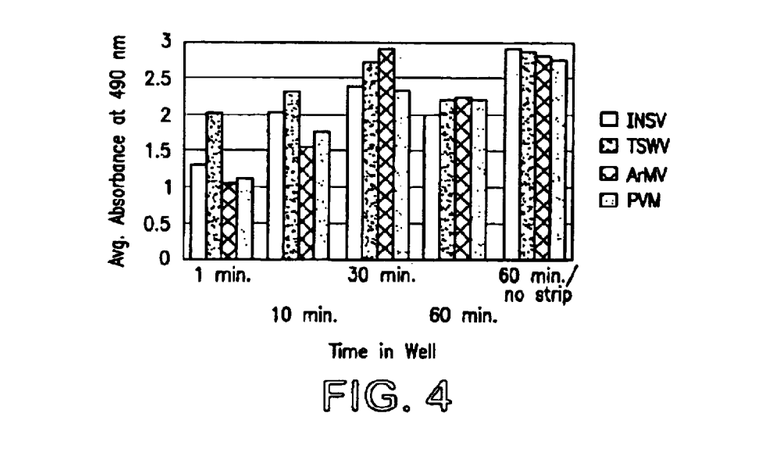
FIG. 4 is a bar chart of the results of ELISAs for detecting various viruses in which control strips comprising nylon pads with the various viruses absorbed thereon were used to deliver the various viruses to the ELISAs by incubating the control strips in extraction buffer for 1, 10, 30, and 60 minutes compared to ELISAs in which the various viruses were delivered by pipetting.

As shown in FIG. 4, the strips residing in the wells for one minute delivered sufficient virus to the well for an ELISA. The results also show that there was more effective delivery of the virus for the longer residence time periods.

EXAMPLE 4

The viruses used in Example 3 are generally known to be stable viruses. In this example, viral controls and standards comprising more labile viruses such as cucumber mosaic virus (CMV) and potyvirus (POTY) were compared to controls and standards comprising the stable tobacco mosaic virus common strain (TMV-c).

Lyophilized CMV, POTY, and TMV infected tissue were each reconstituted in PBS and in distilled water. Then, 10 $\mu$L aliquots were each applied to separate nylon pads pretreated with pretreatment buffer 01 and adhered to plastic card stock as described in Example 1. The nylon pads were dried overnight at room temperature. Afterwards, each was cut into triplicate strips.

Each of the triplicate strips was placed in a well of an ELISA plate containing 100 $\mu$L extraction buffer appropriate for the plant tissue being assayed. As a control, 10 $\mu$L aliquots of the infected tissue suspensions were each pipetted in triplicate wells containing the extraction buffer as well. After about two hours at room temperature, the strips were removed from the wells and the ELISA was performed as usual. The POTY ELISAs were performed using alkaline phosphatase (AP) detection chemistry, while the other ELISAs were performed using peroxidase (PX) detection chemistry. The ELISA plates were scored earlier than the test required to ensure numerical results.

Figure 5:
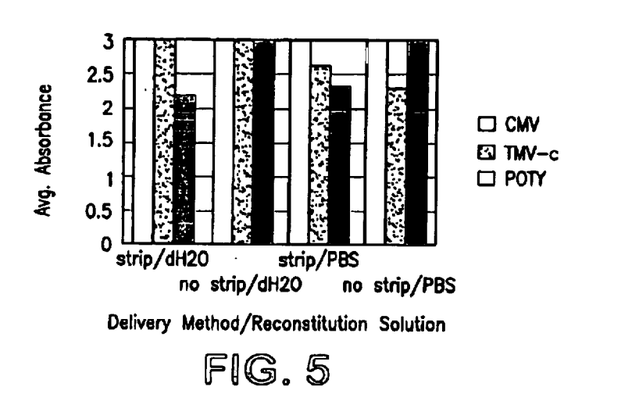
FIG. 5 is a bar chart of the results of ELISAs for detecting various labile viruses in which the ability of control strips comprising nylon pads with the various viruses absorbed thereon to deliver various labile plant viruses to the ELISAs was compared to ELISAs in which the labile viruses were delivered by pipetting.

The results shown in FIG. 5 show that the labile virus controls appeared to be stabilized by drying on nylon pads. A stability study of these nylon pads showed that the CMV and TMV-c were completely stable when stored at either 37° C., room temperature, or 4° C. for at least 248 days. An ELISA well residence time course study with the above strips showed an off-scale absorbance (3.000 or greater) for each of the strips at each of the above time points.

EXAMPLE 5

To determine whether the type of ELISA detection chemistry, either AP or PX, had an affect on the ability of the strips to deliver controls, all of the strips made in Examples 3–4 were evaluated in ELISAs using AP chemistry. In general, the detection chemistry used for a particular plant pathogen depends on the infected plant tissue being used because some plant tissues can interfere with either AP or PX detection chemistry.

Figure 6:
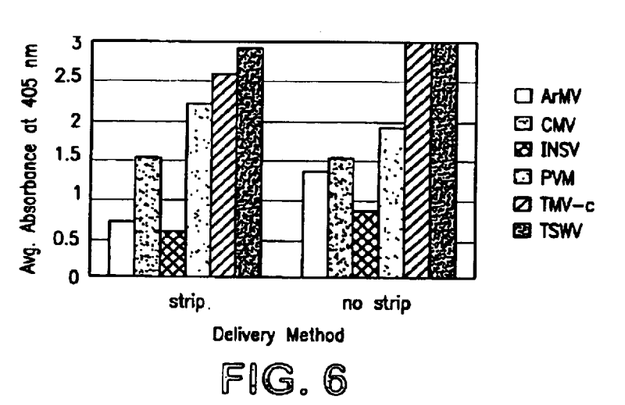
FIG. 6 is a bar chart of the results of ELISAs using AP detection chemistry to detect various viruses in which the effectiveness of control strips comprising nylon pads with the various viruses absorbed thereon to deliver various plant viruses to the ELISAs was compared to ELISAs in which the plant viruses were delivered by pipetting.

The results shown in FIG. 6 show that with the sometimes less sensitive AP detection chemistry, the strips provided sufficient material for either AP or PX assays. The antigen provided by the controls was in the acceptable range of detection for either AP or PX detection chemistry.

EXAMPLE 6

To determine whether the porous carrier material may have an effect on the amount or stability, or both, of infected tissue deposited thereon, three types of glass fiber pads with or without pretreatment were compared to the pretreated nylon pad.

Fresh unlyophilized plum pox virus (PPV) infected tobacco tissue was used. PPV is an unstable virus and an important fruit pathogen. The glass fiber pads that were evaluated were Millipore T9BM0515, Whatman Rapid Q27, and Schleicher & Schuell (S&S) #33. A first set of each glass fiber pad type was pretreated with pretreatment buffer 01 and air dried overnight at room temperature and a second set was left untreated. Strips comprising each glass fiber pad was prepared as in Example 1. The pretreated nylon pads were prepared in the same manner.

A sap was made from the PPV infected tissue by pressing the infected tissue to extrude the sap containing the PPV from the tissue and collecting the sap. The sap was then diluted 1:2 with phosphate buffered saline (PBS). In general, to determine the proper dilution for a particular sap, the sap is serial diluted and the optimal dilution for making controls is determined by ELISA (or the particular assay for which the control is to be used).

The above glass fiber and nylon pads prepared as above were then dipped into the PPV-containing diluted sap. After drying the pads overnight at room temperature, the pads on card stock were cut into strips which were then divided into two lots for each pad type and treatment. The lots were packaged in a foil ziplock envelope with a desiccant and stored at either 37° C. or 4° C. The total number of strips made for this example was 638. After 30 and 90 days of storage, 12 to 18 strips for each pad type were tested in ELISAs. The results are shown in FIGS. 7, 8, and 9.

Figure 7:
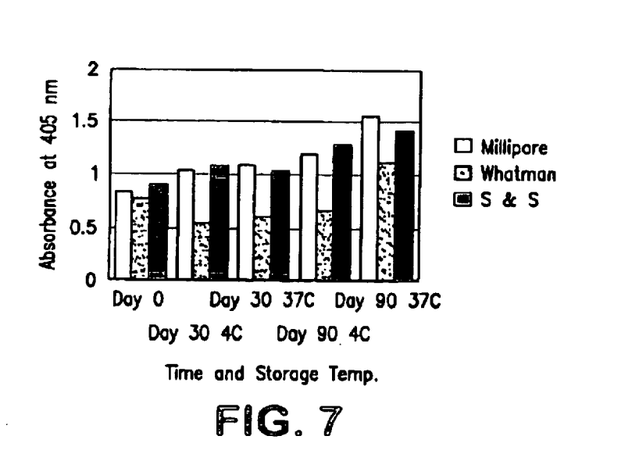
FIG. 7 is a bar chart of the results of ELISAs for detecting PPV in which PPV was delivered to the ELISAs on control strips comprising untreated Millipore T9BM0515 glass fiber, Whatman Rapid Q27 glass fiber, or S&S #33 glass fiber pads with the PPV absorbed thereon which had been stored at 4° C. or 37° C. for 0, 30, or 90 days.
Figure 8:
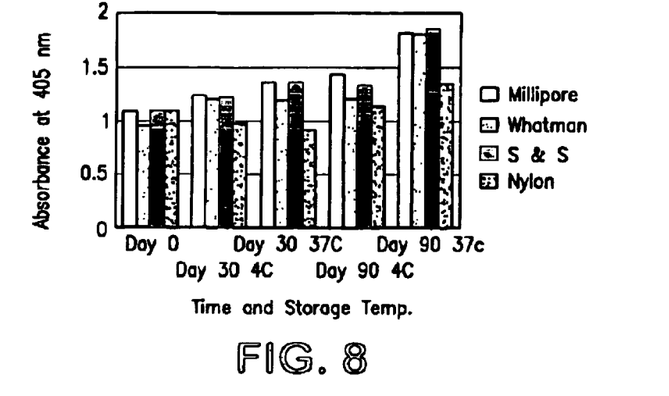
FIG. 8 is a bar chart of the results of ELISAs for detecting PPV in which PPV was delivered to the ELISAs using control strips comprising treated Millipore T9BM0515 glass fiber, Whatman Rapid Q27 glass fiber, S&S #33 glass fiber, or nylon pads with the PPV absorbed thereon which had been stored at 4° C. or 37° C. for 0, 30, or 90 days.
Figure 9:
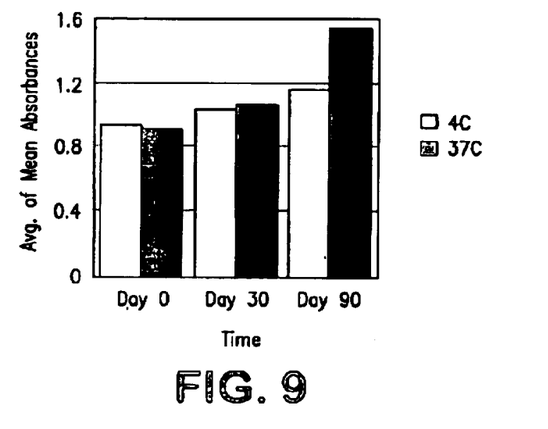
FIG. 9 is a bar chart of the results of ELISAs for detecting PPV in which the PPV was delivered to the ELISAs using control strips comprising glass fiber pads with the PPV absorbed thereon which had been stored at 4° C. or 37° C. for 0, 30, and 90 days.

FIG. 7 shows a comparison of the stability of the PPV on the various untreated pads after 0, 30, and 90 days of storage and FIG. 8 shows a comparison of the stability of the PPV on the various treated pads after 0, 30, and 90 days of storage. The pretreated pads appeared to deliver the viral controls more efficiently than the untreated pads. The pretreated glass fiber pads appeared to deliver more of the viral controls than the pretreated nylon pads. FIG. 9 shows that the unstable PPV remained stabile for at least 90 days under each of the temperature conditions.

EXAMPLE 7

Prototype strips for test kits were manufactured using Millipore GFCP203000 glass fiber pads pretreated with pretreatment buffer 01 and air dried overnight at room temperature. The strips were prepared as in Example 1. Fresh Turkish tobacco (*N. tabacum*) tissue was multiply infected with alfalfa mosaic virus (AMV) or tobacco etch virus (TEV) and fresh cowpea tissue (*Vigna unguiculata* ssp. *unguiculata* cvs Blackeye) was infected with cowpea mosaic virus (CPMV). Diluted sap was made by pressing the infected tissue, collecting the sap, and diluted the sap with lyophilization buffer 01. The strips were prepared by dipping the glass fiber pads in the diluted AMV or TEV sap and then air drying overnight as described in Example 1. The air-dried strips were cut into strips (ten for each virus). An aliquot of each diluted sap was stored at 4° C. and used in triplicate as controls.

Figure 10:
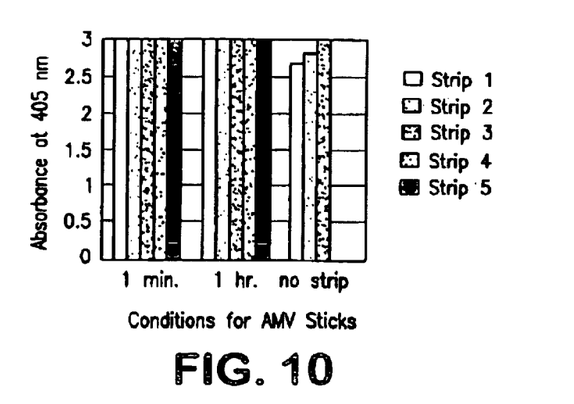
FIG. 10 is a bar chart showing the results of ELISAs for detecting AMV/TEV in which the AMV/TEV were delivered to the ELISAs using control strips comprising Millipore GFCP203000 glass fiber pads and the AMV/TEV absorbed thereon by incubating the control strips in extraction buffer for one minute or one hour compared to ELISAs in which the AMV/TEV was delivered by pipetting.
Figure 11:
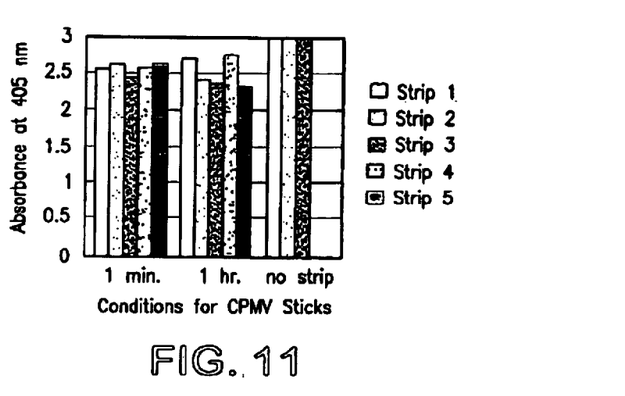
FIG. 11 is a bar chart showing the results of ELISAs for detecting CPMV in which the CPMV was delivered to the ELISAs using control strips comprising Millipore GFCP203000 glass fiber pads with the CPMV absorbed thereon by incubating the control strips in extraction buffer for one minute or one hour compared to ELISAs in which the CPMV was delivered by pipetting.

Five of each set of strips were placed in 100 μL of extraction buffer in ELISA wells for one minute. The glass fiber pad end was cut from the remaining strips and placed in ELISA wells containing extraction buffer for one hour. Afterwards, ELISAs were performed. The results for the glass fiber pads containing AMV are shown in FIGS. 10 and the glass fiber pads containing CPMV are shown in FIG. 11. After one minute in the well, the Millipore glass fiber pads delivered the AMV-infected tissue to the ELISA well as efficiently as the diluted sap controls and delivered CPMV-infected tissue nearly as well as the diluted sap controls. Because TEV was unstable in diluted sap overnight, the TEV control strips were not compared to TEV in solution. However, the TEV dried on control strips remained stable and useful for use as a control.

EXAMPLE 8

Protein standards are sometimes used for ELISAs. In this example, viral PPV coat protein (CP) was produced in *Escherichia coli* containing a plasmid expressing the gene encoding the CP. Such CP expression plasmids are disclosed by Mattanovich et al. in Virus Genes 2: 119–127 (1989) and by Ravelonandro et al. in Gene 120: 167–173 (1992).

S&S #33 glass fiber pads were pretreated with 15% (w/v) sucrose in PBS and air dried over night at room temperature and strips prepared as in Example 1. The glass fiber pads were then dipped in a solution containing 2:1 phosphate buffered saline (PBS) to CP and air dried overnight at room temperature as described in Example 1. After allowing the glass fiber pads on the card blanks to dry overnight, each was cut into strips and divided into four lots. Each lot was individually packaged in a foil ziplock envelope with a desiccant. The envelopes were stored at 37° C., room temperature, 4° C., or −20° C. At various times, two strips from each envelope were tested for stability in ELISAs as described in Examples 1–6.

Figure 12:
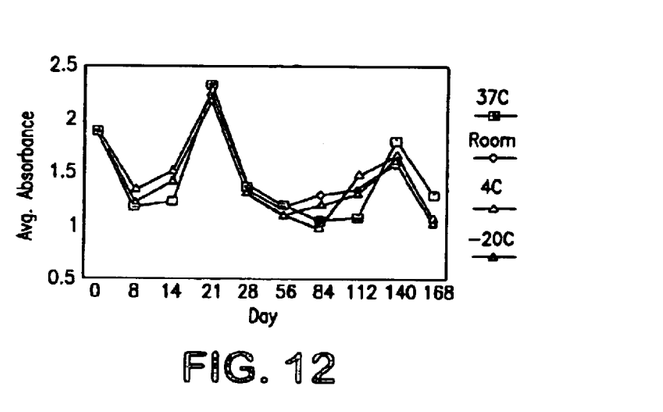
FIG. 12 is a graph showing the results of ELISAs for detecting PPV in which CP was delivered to the ELISAs using control strips comprising Millipore GFCP203000 glass fiber pads with the CP absorbed thereon which had been stored at −20° C., 4° C., or 37° C. for 0 to 168 days.

As shown in FIG. 12, viral CP dried on the strips was stable at all temperatures and over a time period of 168 days. Variations in absorbance were due to variability of the test reagents between lots. The 37° C. data indicates that the strips could be stable for about 5 years.

Figure 13:
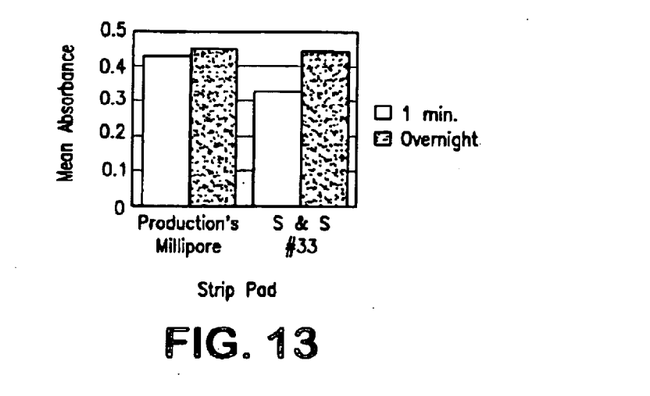
FIG. 13 is a bar chart showing the results of ELISAs for detecting PPV in which CP was delivered to the ELISAs using control strips comprising Millipore GFCP203000 glass fiber pads with the CP absorbed thereon by incubating the control strips in extraction buffer for one minute or overnight compared to ELISAs in which the CP was delivered using control strips comprising S&S #33.

A batch of strips using Millipore GFCP203000 glass fiber pads was pretreated with 15% (w/v) sucrose in PBS as above, dipped in a solution containing 2:1 PBS to CP, and air dried overnight at room temperature. A small batch of strips using S&S #33 glass fiber pads was also prepared with the same CP preparation. Twenty of the Millipore strips were compared to ten of the S&S strips. Half of the strips for each kind were put in ELISA wells containing 100 μL of extraction buffer for one minute and the remaining half of each kind was put into ELISA wells containing 100 μL of extraction buffer overnight. The results shown in FIG. 13 show that there was no significant difference between any of the strip glass fiber pads with overnight delivery.

The PPV CP strips were used in the Agdia's (licensee) testing service's participation in a 2002 seasonal survey of fruit trees. The testing service used a PPV ELISA test kit distributed by Agdia. The antibody coated ELISA plates used to capture the virus were not provided with the kit because the plates must be prepared every 2 to 3 days. Several people were involved in coating the ELISA plates over the testing season. Several people with a variety of testing skills and under the control of or in cooperation with Agdia used the PPV CP strips with the above antibody coated ELISA plates during the seasonal survey. A total of 187 strips were used with an average ELISA absorbance of 0.949. The absorbance range was 0.248 to 2.520. While the amount of CP eluted from the control strips was not uniform, enough CP was eluted from each of the strips to demonstrate that the control strips were be useful for ELISAS.

EXAMPLE 9

Protein standards are sometimes used for ELISAs for detecting markers for transgenic plants. Neomycin phosphotransferase II (NPTII), is one such genetic marker used for selecting transgenic plants.

S&S #33 glass fiber pads were pretreated with 15% (w/v) sucrose in PBS and air dried over night at room temperature. The glass fiber pads were adhered to the adhesive end of plastic card stock. Then, phosphate buffered saline containing 10 or 20 ng/12 μL of NPTII glass fiber pads was pipetted to the pads and the pads air dried overnight at room temperature. After allowing the glass fiber pads on the card blanks to dry overnight, each was cut into strips. Four or six strips for each concentration was tested in ELISAs as described in Examples 1–6. The results are shown in Table 1. In each case, the strips were able to deliver sufficient NPTII for ELISAs.

TABLE 1

| No. of Strips Tested | NPTII Concentration (ng) | Average Absorbance |
| --- | --- | --- |
| 4 | 20 | 1.685 |
| 4 | 10 | 1.171 |
| 6 | 20 | 2.563 |
| 6 | 20 | 3.000 |
| 6 | 20 | 3.000 |

EXAMPLE 10

This example shows that the virus eluted from the glass fiber pads does not pose a significant risk of infection.

Fresh diluted sap from TEV-infected *N. tabacum* tissue was dried onto S&S #33 glass fiber pads and made into strips as described in Example 1. Six of the strips were each soaked in 200 μL of PBS for 30 minutes. The solution was then diluted 1:1 with inoculation buffer and used to inoculate a *N. tabacum* leaf on a seedling. Only two leaves of the seedling were used. Three strips without infected sap were processed as above and used to infected leaves of a seedling. After 20 days of growth, none of the plant leaves became infected with the TEV.

The above was repeated with fresh diluted sap from AMV-infected *N. tabacum* was also prepared as above and used to infect leaves of an *N. tabacum* seedling. None of the leaves became infected after 18 days of growth.

Surprisingly, our method rendered the above viruses noninfectious. The results indicate that the viral controls of the present invention prepared as taught herein are safe and do not present a significant risk that the user of the controls might inadvertently transmit disease to healthy plants. However, while this Example demonstrates that particular viruses prepared as taught herein are rendered noninfectious, it is to be understood that there may be particular viruses which will require an inactivation step using an inactivating agent or process or there may be particular viruses which regulatory agencies require to be inactivated using an inactivating agent or process.

The results further indicate that for most plant viruses, the controls can be made without the need for deliberately inactivating the virus either before or after the virus is absorbed to the glass fiber pad.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

I claim:

1. A method for performing a solution assay for determining whether a test sample contains an analyte, which comprises:
    (a) providing at least one porous support impregnated with a known sample of the analyte so that the analyte remains detectable over time when eluted from the porous support;
    (b) providing a sample to be tested for the presence of the analyte;
    (c) contacting the impregnated porous support with a buffer for a time sufficient to elute analyte from the porous support to provide a control sample for the assay;
    (d) performing the assay with the eluted control sample and separately with the test sample in the buffer; and
    (e) determining whether the test sample contains the analyte by comparing the assay results produced by the test sample to the results produced by the control sample wherein the results indicate that the test sample contains the analyte.

2. The method of claim 1 wherein the porous support comprises a material selected from the group consisting of nylon and glass fiber.

3. The method of claim 1 wherein the porous support is adhered to a surface of a first end of a planar support member having a first end and an opposite end.

4. The method of claim 3 wherein the support member comprises a polymer.

5. The method of claim 3 wherein the porous support adhered to the surface of the support member is cut into strips.

6. The method of claim 1 wherein the analyte is a plant pathogen.

7. The method of claim 6 wherein the plant pathogen is obtained from the sap of a plant infected with the pathogen.

8. The method of claim 6 wherein the plant pathogen is inactivated.

9. The method of claim 1 wherein the analyte is a recombinant protein produced by a transgenic plant.

10. The method of claim 9 wherein the recombinant protein is selected from the group consisting of Bt-Cry1Ac, Bt-CryAb, Bt-Cry3A, Bt-Cry9C, and neomycin phosphotransferase.

11. The method of claim 1 wherein the analyte comprises at least one protein from eggs of a plant pest.

12. The method of claim 11 wherein the plant pest is selected from the group consisting of cotton bollworm and tobacco budworm.

13. The method of claim 1 wherein the analyte is a hormone.

14. The method of claim 13 wherein the hormone is a plant hormone selected from the group consisting of abscisic acid, dihydrozeatin riboside, indole-3-acetic acid, isopentenyladenosine, and trans-zeatin riboside.

15. The method of claim 1 wherein the analyte is an isolated protein from a pathogen selected from the group consisting of bacteria, fungi, virus, and pest.

16. The method of claim 15 wherein the pathogen is a plant pathogen.

17. The method of claim 15 wherein the isolated protein is a recombinant protein produced in a bacterium.

18. The method of claim 1 wherein the analyte is an antigen or metabolite produced by a cancer cell.

19. The method of claim 1 wherein the analyte is an antigen or metabolite produced by a patient with an autoimmune disease.

20. The method of claim 1 wherein the assay is an immunoassay selected from the group consisting of ELISA, immunoprecipitation, immunodiffusion, radioimmunoassay, immunofluorescence, and lateral flow.

21. The method of claim 1 wherein the porous support is removed from the buffer after the analyte has been eluted from the porous support.

22. The method of claim 1 wherein the control sample and the test sample are serially diluted to provide a series of dilutions for the assay.

* * * * *